(12) United States Patent
Yoshida

(10) Patent No.: US 10,456,399 B2
(45) Date of Patent: Oct. 29, 2019

(54) METHOD FOR TREATING CANCER PATIENTS WITH SEVERE RENAL IMPAIRMENT

(71) Applicant: TAIHO PHARMACEUTICAL CO., LTD., Chiyoda-ku (JP)

(72) Inventor: Kenichiro Yoshida, Tsukuba (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 16/054,073

(22) Filed: Aug. 3, 2018

(65) Prior Publication Data

US 2018/0338976 A1 Nov. 29, 2018

Related U.S. Application Data

(63) Continuation of application No. PCT/JP2017/003994, filed on Feb. 3, 2017.

(60) Provisional application No. 62/291,799, filed on Feb. 5, 2016.

(51) Int. Cl.
*A61K 31/513* (2006.01)
*A61K 31/506* (2006.01)
*A61K 31/7072* (2006.01)
*A61P 13/12* (2006.01)
*A61P 35/00* (2006.01)

(52) U.S. Cl.
CPC .......... *A61K 31/513* (2013.01); *A61K 31/506* (2013.01); *A61K 31/7072* (2013.01); *A61P 13/12* (2018.01); *A61P 35/00* (2018.01)

(58) Field of Classification Search
CPC ............................ C07D 401/12; A61K 31/513
See application file for complete search history.

(56) References Cited

U.S. PATENT DOCUMENTS

| 5,744,475 A | 4/1998 | Yano et al. | |
| 7,799,783 B2 * | 9/2010 | Emura | A61K 31/513 514/235.8 |
| 9,371,380 B2 * | 6/2016 | Ito | C12Q 1/6886 |
| 2014/0213602 A1 * | 7/2014 | Ito | C12Q 1/6886 514/274 |
| 2016/0082032 A1 * | 3/2016 | Sakamoto | A61K 31/513 514/50 |

FOREIGN PATENT DOCUMENTS

| EP | 1 849 470 A1 | 10/2007 |
| WO | WO 1996/30346 | 10/1996 |

OTHER PUBLICATIONS

Doi et al., British Journal of Cancer, 2012, 107:429-434.*
Hurria et al., Drugs Aging, 2005, 22(9): 785-791.*
English language translation only of International Search Report dated Mar. 7, 2017 in corresponding PCT application No. PCT/JP2017/003994, 1 page.
Overman et al., "Phase 1 study of TAS-102 administered once daily on a 5-day-per-week schedule in patients with solid tumors", Invest New Drugs, 26(5):, 2008, 445-454.
Yoshino et al., "TAS-102 monotherapy for pretreated metastatic colorectal cancer: a double-blind, randomised, placebo-controlled phase 2 trial", Lancet Oncol. 13 (10):, 2012, 993-1001.
"Shin Iyakuhin no 'Shiyojo no Chui' no Kaisetu, Lonsurf (registered trademark) Haigojo T15 • T20", Taiho Pharmaceutical Co., Ltd., revised Apr. 2015, 9 pages.
"Tenpu Bunsho, TS-1 (registered trademark) Haigo capsule T20 • T25, Haigo Karyu T20 • T25", Taiho Pharmaceutical Co., Ltd., 29th edition, 2014, 7 pages.
Mayer et al., "Randomized Trial of TAS-102 for Refractory Metastatic Colon Cancer", The New England Journal of Medicine, May 14, 2015, pp. 1909-1919.
"Protocol No. TPU-TAS-102-301", Taiho Pharmaceutical Co., Ltd; Taiho Oncology Inc., 2014, 448 pages.
"A Phase I Study of TAS-102 in Patients With Advanced Solid Tumors With Renal Impairment", ClinicalTrials.gov (downloaded from https://www.clinicaltrials.gov/ct2/show/NCT02301117?term=TAS-102+renal&rank=1), 2017, 8 pages.
"Lonsurf (TAS-102), combination product of trifluridine and tipiracil hydrochloride at a molar ratio of 1: 0.5", Clinical Pharmacology and Biopharmaceutics Review(s), Dec. 19, 2015, pp. 1-65, XP055613686.
Munar et al., "Drug Dosing Adjustments in Patients with Chronic Kidney Disease", AM Fam Physician, May 15, 2007, pp. 1487-1496, XP055410272.
Doogue et al., "Drug Dosing in Renal Disease", Clin Biochem Rev, vol. 32, May 1, 2011, pp. 69-73, XP055613691.
Booka et al., "Development of an S-1 dosage formula based on renal function by a prospective pharmacokinetic study", Gastric Cancer, Springer Japan, Tokyo, vol. 19, No. 3, Aug. 25, 2015, pp. 876-886, XP035976852.
Hong et al., "Phase 1 Study to Determine the Safety and Pharmacokinetics of Oral Administration of TAS-102 in Patients With Solid Tumors", Cancer, vol. 107, No. 6, Jan. 1, 2006, pp. 1383-1390, XP055144969.
Extended European Search Report dated Aug. 27, 2019, in European Patent Application No. 17747563.9, filed Feb. 3, 2017.

* cited by examiner

*Primary Examiner* — Rei Tsang Shiao
(74) *Attorney, Agent, or Firm* — Oblon, McClelland, Maier & Neustadt, L.L.P.

(57) ABSTRACT

A method for treating cancer in patients with creatinine clearance of 15 mL/min or more and less than 30 mL/min, including dividing a combination drug containing α,α,α-trifluorothymidine (FTD) and 5-chloro-6-[(2-iminopyrrolidine-1-yl)methyl]pyrimidine-2,4(1H,3H)-dione hydrochloride in a molar ratio of 1:0.5, in a dose of 30 to 50 mg/m$^2$/day as FTD-equivalent, into two to four times a day, and orally administering it to the patient.

30 Claims, 1 Drawing Sheet

RELATIONSHIP BETWEEN CREATININE CLEARANCE
AND ORAL CLEARANCE OF FTD
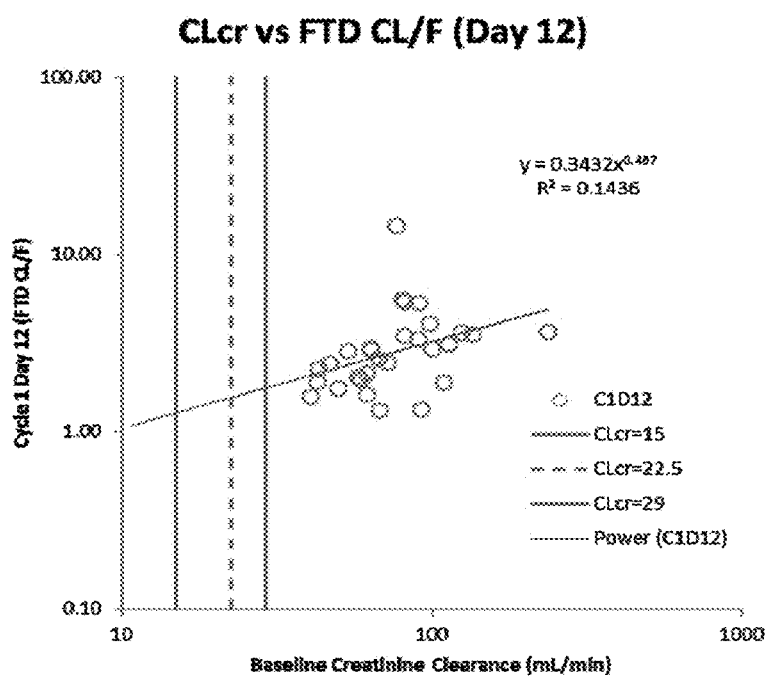

METHOD FOR TREATING CANCER PATIENTS WITH SEVERE RENAL IMPAIRMENT

CROSS-REFERENCE TO RELATED APPLICATIONS

The present application is a continuation of International Application No. PCT/JP2017/003994, filed Feb. 3, 2017, which is based upon and claims the benefits of priority to U.S. Provisional Application No. 62/291,799, filed Feb. 5, 2016. The entire contents of these applications are incorporated herein by reference.

FIELD OF THE INVENTION

The present invention relates to a method for treating cancer patients with severe renal impairment.

BACKGROUND OF THE INVENTION

Trifluridine (also known as: $\alpha,\alpha,\alpha$-trifluorothymidine; hereinafter, also referred to as "FTD") exhibits an antitumor effect by DNA synthesis inhibition by thymidylate production-inhibiting action and DNA function inhibition by incorporation into DNA. Tipiracil hydrochloride (chemical name: 5-chloro-6-[(2-iminopyrrolidine-1-yl)methyl]pyrimidine-2,4(1H, 3H)-dione hydrochloride; hereinafter, also referred to as "TPI") has inhibitory effect against thymidine phosphorylase. It is known that TPI suppresses the decomposition of FTD by thymidine phosphorylase in the living body, thereby potentiating the antitumor effect of FTD (Patent Literature 1).

Currently, a combination drug containing FTD and TPI in a molar ratio of 1:0.5 (hereinafter also referred to as "FTD/TPI combination drug") is under development as a therapeutic agent for a solid cancer. It was approved as a therapeutic agent for advanced and recurrent colorectal cancer in the U.S., as a trade name, LONSURF® (trifluridine and tipiracil) tablets (Non-patent Literature 1 and 2). The dosage and administration of the FTD/TPI combination drug in a clinical practice are typically, for adults, based on the body surface area, 70 mg/m²/day as FTD-equivalent is orally administered twice a day for 5 consecutive days, followed by rest for 2 days. This procedure is repeated twice, and followed by rest for 14 days. It is defined that the administration is repeated with the above procedure as one cycle.

TPI is a renal excretory drug, thus it is theoretically considered that, when the FTD/TPI combination drug is administered to the patients with impaired renal function, exposure to FTD can be increased. Also in a clinical trial, as a result of comparing the incidence of adverse events among the levels of renal impairment, based on the creatinine clearance (hereinafter, also referred to as "CLcr") value of the patients who had the FTD/TPI combination drug, it is recognized that the incidence of side effects related to myelosuppression (decrease in platelet count, decrease in erythrocyte count, decrease in hemoglobin, decrease in neutrophil count) tends to be higher in mild renal impairment (CLcr: 60 to 89 mL/min) and moderate renal impairment (CLcr: 30 to 59 mL/min), as compared to normal renal function (CLcr: ≥90 mL/min). The creatinine clearance (CLcr) value of the patient is calculated using Cockcroft-Gault equation, and classified based on the classification criteria of renal function in the Food and Drug Administration (FDA), Guidance for Industry, Pharmacokinetics in Patients with Impaired Renal Function—Study Design, Data Analysis, and Impact on Dosing and Labeling. Therefore, the patients with severe renal impairment (CLcr: 15 to 29 mL/min) have not been applicable, thus the FTD/TPI combination drug is not administered to the patient either in the clinical trial performed so far, and there is no information of safety and efficacy.

Generally, it is necessary to adjust the dose or dosing interval depending on the degree of renal function in drug administration to the patients with renal impairment, and it is recommended to select the dose based on pharmacokinetics (PK) according to the FDA guidance.

However, it is not easy to perform cancer treatment that is safer and has high effectiveness on a cancer patient with severe renal impairment.

NON-PATENT LITERATURE

[Non-patent Literature 1] Invest New Drugs 26(5): 445-54, 2008
[Non-patent Literature 2] Lancet Oncol. 13 (10):993-1001, 2012

PATENT LITERATURE

[Patent Literature 1] WO 1996/30346

SUMMARY OF THE INVENTION

The present invention relates to provision of a method for treating cancer of cancer patients with severe renal impairment.

The present inventor has tried cancer treatment by an FTD/TPI combination drug on cancer patients with severe renal impairment with CLcr of 15 to 29 mL/min, and found that, when a dose of 30 to 50 mg/m² a day as FTD-equivalent is divided into two to four times a day and orally administered, a remarkable anticancer effect is recognized while avoiding severe side effects.

That is, the present invention provides the following inventions [1] to [28]:

[1] A method for treating cancer in patients with creatinine clearance of less than 30 mL/min, including dividing a combination drug containing $\alpha,\alpha,\alpha$-trifluorothymidine (FTD) and 5-chloro-6-[(2-iminopyrrolidine-1-yl)methyl]pyrimidine-2,4(1H,3H)-dione hydrochloride in a molar ratio of 1:0.5, in a dose of 30 to 50 mg/m²/day as FTD-equivalent, into two to four times a day, and orally administering it to the patient;
[2] The method for treating cancer according to [1], where the patient is a patient with a creatinine clearance of 15 mL/min or more and 29 mL/min or less;
[3] The method for treating cancer according to [1] or [2], where a dose of 40 mg/m²/day as FTD-equivalent is divided into twice a day and orally administered;
[4] The method for treating cancer according to any one of [1] to [3], where the administration schedule is 5-day consecutive oral administrations and 2-day rest, per week;
[5] The method for treating cancer according to any one of [1] to [4], where an administration schedule of 5-day consecutive oral administrations and 2-day rest are repeated twice, followed by rest for 14 days; and
[6] The method for treating cancer according to any one of [1] to [5], where the cancer is gastrointestinal cancer or breast cancer.
[7] The method for treating cancer according to any one of [1] to [6], wherein the cancer is large bowel cancer.

[8] A therapeutic agent for treating cancer in patients with creatinine clearance of less than 30 mL/min, wherein a combination drug containing α,α,α-trifluorothymidine (FTD) and 5-chloro-6-[(2-iminopyrrolidine-1-yl)methyl]pyrimidine-2,4(1H,3H)-dione hydrochloride in a molar ratio of 1:0.5 is orally administered to the patient in a dose of 30 to 50 mg/m$^2$/day as FTD-equivalent by being divided into two to four times a day.
[9] The therapeutic agent according to [8], wherein the patient is a patient with a creatinine clearance of 15 mL/min or more and 29 mL/min or less.
[10] The therapeutic agent according to [8] or [9], wherein a dose of 40 mg/m$^2$/day as FTD-equivalent is divided into twice a day and orally administered.
[11] The therapeutic agent according to any one of [8] to [10], wherein the administration schedule is 5-day consecutive oral administrations and 2-day rest, per week.
[12] The therapeutic agent according to any one of [8] to [11], wherein an administration schedule of 5-day consecutive oral administrations and 2-day rest are repeated twice, followed by rest for 14 days.
[13] The therapeutic agent according to any one of [8] to [12], wherein the cancer is gastrointestinal cancer or breast cancer.
[14] The therapeutic agent according to any one of [8] to [13], wherein the cancer is large bowel cancer.
[15] Use of a combination drug containing α,α,α-trifluorothymidine (FTD) and 5-chloro-6-[(2-iminopyrrolidine-1-yl)methyl]pyrimidine-2,4(1H,3H)-dione hydrochloride in a molar ratio of 1:0.5 for the production of a therapeutic agent for treating cancer in patients with creatinine clearance of less than 30 mL/min, wherein the combination drug is orally administered to the patient in a dose of 30 to 50 mg/m$^2$/day as FTD-equivalent by being divided into two to four times a day.
[16] The use according to [15], wherein the patient is a patient with a creatinine clearance of 15 mL/min or more and 29 mL/min or less.
[17] The use according to [15] or [16], wherein a dose of 40 mg/m$^2$/day as FTD-equivalent is divided into twice a day and orally administered.
[18] The use according to any one of [15] to [17], wherein the administration schedule is 5-day consecutive oral administrations and 2-day rest, per week.
[19] The use according to any one of [15] to [18], wherein an administration schedule of 5-day consecutive oral administrations and 2-day rest are repeated twice, followed by rest for 14 days.
[20] The use according to any one of [15] to [19], wherein the cancer is gastrointestinal cancer or breast cancer.
[21] The use according to any one of [15] to [20], wherein the cancer is large bowel cancer.
[22] A combination drug containing α,α,α-trifluorothymidine (FTD) and 5-chloro-6-[(2-iminopyrrolidine-1-yl) methyl]pyrimidine-2,4(1H,3H)-dione hydrochloride in a molar ratio of 1:0.5 for treating cancer in patients with creatinine clearance of less than 30 mL/min, wherein the combination drug is orally administered to the patient in a dose of 30 to 50 mg/m$^2$/day as FTD-equivalent by being divided into two to four times a day.
[23] The combination drug according to [22], wherein the patient is a patient with a creatinine clearance of 15 mL/min or more and 29 mL/min or less.
[24] The combination drug according to [22] or [23], wherein a dose of 40 mg/m$^2$/day as FTD-equivalent is divided into twice a day and orally administered.
[25] The combination drug according to any one of [22] to [24], wherein the administration schedule is 5-day consecutive oral administrations and 2-day rest, per week.
[26] The combination drug according to any one of [22] to [25], wherein an administration schedule of 5-day consecutive oral administrations and 2-day rest are repeated twice, followed by rest for 14 days.
[27] The combination drug according to any one of [22] to [26], wherein the cancer is gastrointestinal cancer or breast cancer.
[28] The method for treating cancer according to any one of [22] to [27], wherein the cancer is large bowel cancer.

Effect of the Invention

According to the treatment method of the present invention, an excellent effect of treating cancer of cancer patients with severe renal impairment is obtained without causing severe side effects.

BRIEF DESCRIPTION OF DRAWINGS

FIG. 1 is a graph showing a relationship between creatinine clearance and oral clearance of FTD on Day 12 after administration.

DETAILED DESCRIPTION OF THE INVENTION

In the present invention, a combination drug containing α,α,α-trifluorothymidine and 5-chloro-6-[(2-iminopyrrolidine-1-yl)methyl]pyrimidine-2,4(1H,3H)-dione hydrochloride in a molar ratio of 1:0.5 is used.

FTD and TPI are each known compounds, and can be synthesized, for example, according to a method described in WO 1996/30346. Also, a FTD/TPI combination drug is publicly known (Non Patent Literatures 1 and 2). In addition, the FTD/TPI combination drug in a tablet formulation was approved as a therapeutic agent for advanced and recurrent colorectal cancer in the U.S.

The FTD/TPI combination drug used in the present invention should be in an orally-administrable formulation. Examples of the formulation include tablets, coated tablets, pills, powders, granules, capsules, solutions, suspensions, and emulsions. These preparations can be formulated by a conventional formulation method commonly known in the art, for example, using a pharmaceutically acceptable carrier.

Also, it is possible to properly divide and package the FTD/TPI combination drug, so as to divide a dose of 30 to 50 mg/m$^2$/day into two to four times a day and administer it. The packaging method is not particularly limited so long as it is a conventional packaging method commonly known in the art. For example, tablets can be packaged in a moisture proof and deoxygenated packaging material.

Examples of the pharmaceutically acceptable carrier include various ones which are commonly used in conventional drugs, such as excipients, binders, disintegrators, lubricants, disintegration inhibitors, absorption promoters, humectants, adsorbents, coating agents, solvents, solubilizers, suspending agents, isotonic agents, pH adjusting agents, buffering agents, stabilizers, coloring agents, flavoring agents, and odor improving agents.

Examples of the excipients include lactose, sucrose, D-mannitol, starch, crystalline cellulose, and calcium silicate.

Examples of the binders include hydroxypropylcellulose, methylcellulose, polyvinylpyrrolidone, maltose syrup powder, and hypromellose.

Examples of the disintegrators include starch, sodium glycolate, carmellose calcium, croscarmellose sodium, crospovidone, low substituted hydroxy-propylcellulose, and partially pregelatinized starch.

Examples of the lubricants include talc, magnesium stearate, sucrose fatty acid ester, stearic acid, and sodium stearyl fumarate.

Examples of the disintegration inhibitors include sucrose, stearic acid, cacao butter, and hydrogenated oil.

Examples of the absorption promoters include a quaternary ammonium base and sodium lauryl sulfate.

Examples of the humectants include glycerin and starch.

Examples of the adsorbents include starch, lactose, kaolin, bentonite, and colloidal silicic acid.

Examples of the coating agents include ethylcellulose, aminoalkyl methacrylate copolymer RS, hypromellose, and sucrose.

Examples of the solvents include water, propylene glycol, and physiological saline.

Examples of the solubilizers include polyethylene glycol, ethanol, α-cyclodextrin, macrogol 400, and polysorbate 80.

Examples of the suspending agents include carrageenan, a crystalline cellulose-carmellose sodium, and polyoxyethylene hydrogenated castor oil.

Examples of the isotonic agents include sodium chloride, glycerin, and potassium chloride.

Examples of the pH adjusting agents and buffering agents include sodium citrate, hydrochloric acid, lactic acid, phosphoric acid, and sodium dihydrogen phosphate.

Examples of the stabilizers include sodium pyrosulfite, edetate sodium, erythorbic acid, magnesium oxide, and dibutylhydroxytoluene.

Examples of the coloring agents include titanium oxide, iron sesquioxide, Food Blue No. 1, and copper chlorophyll.

Examples of the flavoring and odor improving agents include aspartame, saccharin, sucralose, 1-menthol, and mint flavor.

In the present invention, the FTD/TPI combination drug in a dose of 30 to 50 mg/m$^2$/day as FTD-equivalent is divided into two to four times a day and orally administered.

The dose of the FTD/TPI combination drug is 30 to 50 mg/m$^2$/day, preferably 30 to 48 mg/m$^2$/day, preferably 35 to 45 mg/m$^2$/day, and preferably 40 mg/m$^2$/day, as FTD-equivalent.

In addition, the number of administration per day is two to four times, preferably two to three times, and more preferably twice.

The interval between administrations is preferably 6 hours or more.

Here, the dose to patients is determined based on the body surface area (BSA) calculated from the patient's height and body weight. As a method for calculating a body surface area, a conventional method is appropriately used, depending on, for example, the race, sex, health condition and symptom of the patient, for example, the following calculation formulae 1 to 6, and preferably the following 1 or 2(a).

1. The Mosteller formula (See N Engl J Med 1987 Oct. 22; 317(17): 1098 (letter))

$$\text{BSA (m}^2\text{)} = ([\text{Height (cm)} \times \text{Weight (kg)}]/3600)^{1/2}$$

2. The DuBois and DuBois formula (See Arch Int Med 1916 17: 863-71; J Clin Anesth. 1992; 4(1): 4-10)

(a) $\text{BSA (m}^2\text{)} = 0.20247 \times \text{Height (m)}^{0.725} \times \text{Weight (kg)}^{0.425}$ (b) $\text{BSA (m}^2\text{)} = 0.007184 \times \text{Height (cm)}^{0.725} \times \text{Weight (kg)}^{0.425}$ 3. The Haycock formula (See The Journal of Pediatrics 1978 93: 1: 62-66)

$$\text{BSA (m}^2\text{)} = 0.024265 \times \text{Height (cm)}^{0.3964} \times \text{Weight (kg)}^{0.5378}$$

4. The Gehan and George formula (See Cancer Chemother Rep 1970 54: 225-35)

$$\text{BSA (m}^2\text{)} = 0.0235 \times \text{Height (cm)}^{0.42246} \times \text{Weight (kg)}^{0.51456}$$

5. The Boyd formula (See Minneapolis: university of Minnesota Press, 1935)

$$\text{BSA (m}^2\text{)} = 0.0003207 \times \text{Height (cm)}^{0.3} \times \text{Weight (gram)}^{(0.7285-(0.0188 \times LOG \text{ (gram)}))}$$

6. The Fujimoto formula (See Nihon Eiseigaku Zasshi, 1968 23(5): 443-450)

$$\text{BSA (m}^2\text{)} = 0.008883 \times \text{Height (cm)}^{0.663} \times \text{Weight (kg)}^{0.444}$$

For example, when the body surface area of a cancer patient of 175 cm in height and 70 kg in weight is calculated using the above calculation formula 1, the body surface area is calculated as $([175 \text{ (cm)} \times 70 \text{ (kg)}]/3600)^{1/2} = 1.84$ (m$^2$). When the dose is 50 mg/m$^2$/day as FTD-equivalent in the patient, the total daily dose is calculated as 1.84×50=92 mg, and set to about 92 mg.

In the present invention, the subject to be administered is a cancer patient with CLcr of less than 30 mL/min, more preferably, a cancer patient with CLcr of 15 mL/min or more and less than 30 mL/min, and particularly preferably, a cancer patient with CLcr of 15 mL/min or more and 29 mL/min or less.

The value of CLcr of the patient is an index of renal function, and the patients with CLcr of 15 to 29 mL/min include the patients with severe renal impairment (patient with severe renal dysfunction). The patient with severe renal impairment is also referred to as advanced renal dysfunction.

In the present invention, CLcr is calculated using Cockcroft-Gault equation shown below.

[Cockcroft-Gault Equation]

$$\text{Male: CLcr (mL/min)} = \{(140-\text{age}) \times \text{Weight (kg)}\}/\{\text{value of serum creatinine (mg/dL)} \times 72\}$$

$$\text{Female: CLcr (mL/min)} = \{(140-\text{age}) \times \text{Weight (kg)}\}/\{\text{value of serum creatinine (mg/dL)} \times 72\} \times 0.85$$

Here, the value of serum creatinine can be measured by a conventional method.

In the present invention, the administration schedule is preferably orally administered for 5 consecutive days, followed by rest for 2 days, per week. It is also preferred that 5-day consecutive oral administrations and 2-day rest are repeated twice, followed by rest for 14 days, and the administration is repeated with this procedure as one cycle.

Examples of the cancer to be a target of the treatment method of the present invention include head and neck cancer, gastrointestinal cancer (e.g., esophageal cancer, gastric cancer, duodenal cancer, liver cancer, biliary tract cancer (gallbladder/bile duct cancer), pancreatic cancer, small intestinal cancer, large bowel cancer (colorectal cancer, colon cancer, rectal cancer)), lung cancer (non-small cell lung cancer, small cell lung cancer), breast cancer, ovarian cancer, uterine cancer (cervical cancer, endometrial cancer), renal cancer, bladder cancer, prostate cancer, and skin cancer. The cancer includes not only a primary tumor but also a tumor derived from a solid cancer that has metastasized to other organs (such as liver). Among them, from the viewpoint of antitumor effects and side effects, the target of the treatment method of the present invention is preferably head and neck cancer, gastrointestinal cancer, lung cancer, breast cancer, renal cancer and skin cancer, more preferably gastrointestinal cancer or breast cancer, more preferably esophageal cancer, large bowel cancer and gastric cancer, and especially preferably large bowel cancer. The treatment method of the present invention may be postoperative adjuvant chemotherapy that is performed for preventing the recurrence after having extracted the tumor surgically, and also may be preoperative adjuvant chemotherapy that is performed in advance for extracting the tumor surgically.

EXAMPLES

Next, the present invention will be explained in further detail by way of examples. However, this invention should not be limited to these examples in any manner, and many variations are possible by a person with ordinary skill in the art within the technical idea of the present invention.

(Example 1) Dose Estimation in Cancer Patients with Severe Renal Impairment

Pharmacokinetic of FTD was studied in patients with solid cancer including colorectal cancer, when performing a treatment of repeating an administration schedule of orally administering an FTD/TPI combination drug (mixture of FTD and TPI in a molar ratio of 1:0.5) in 35 mg/m² per once (as FTD, the same applies hereinafter) for 5 consecutive days twice a day, followed by rest for 2 days twice, followed by rest for 14 days, and repeating this procedure as one cycle.

Renal function was evaluated by calculating the value of CLcr by the Cockcroft-Gault equation before start of administration, and the patients were assigned into groups of control (normal, CLcr: ≥90 mL/min), mild (CLcr: 60 to 89 mL/min) and moderate (CLcr: 30 to 59 mL/min). Blood collection was performed after administration of the FTD/TPI combination drug on Day 1 and Day 12, at predose and at 0.5, 1, 2, 4, 6, 8, 10, 12 hours after administration, and FTD and TPI concentrations in plasma were measured. Pharmacokinetic parameters of FTD and TPI were calculated using the resulting concentrations in the plasma, and the results were shown in Table 1.

TABLE 1

Pharmacokinetic parameters of FTD and TPI
(Cohort 0: normal, Cohort 1: mild renal impairment, Cohort 2: moderate renal impairment)

| Compound | Cohort | Subject | Day 1 | | | | Day 12 | | | |
| --- | --- | --- | --- | --- | --- | --- | --- | --- | --- | --- |
| | | | $C_{max}$ (ng/mL) | $AUC_{0-12}$ (hr * ng/mL) | $t_{1/2}$ (hr) | CL/F (L/hr) | $C_{max}$ (ng/mL) | $AUC_{0-12}$ (hr * ng/mL) | $t_{1/2}$ (hr) | CL/F (L/hr) |
| FTD | 0 | N | 10 | 10 | 10 | 10 | 10 | 10 | 10 | 10 |
| | | Mean | 2882 | 7873 | 1.26 | 8.72 | 5235 | 20124 | 2.09 | 3.29 |
| | | SD | 1372 | 2819 | 0.38 | 4.20 | 2662 | 7395 | 0.67 | 1.12 |
| | | CV % | 47.6 | 35.8 | 30.1 | 48.1 | 50.9 | 36.7 | 32.0 | 33.9 |
| | 1 | N | 12 | 12 | 12 | 12 | 11 | 11 | 11 | 11 |
| | | Mean | 3161 | 7292 | 1.79 | 10.08 | 4667 | 23383 | 2.40 | 4.1 |
| | | SD | 1363 | 2634 | 0.49 | 5.95 | 2676 | 13634 | 0.75 | 3.71 |
| | | CV % | 43.1 | 36.1 | 27.5 | 59.0 | 57.3 | 58.3 | 31.3 | 90.6 |
| | 2 | N | 11 | 11 | 11 | 11 | 10 | 8 | 8 | 8 |
| | | Mean | 2763 | 8135 | 1.90 | 9.17 | 6014 | 30405 | 3.22 | 2.1 |
| | | SD | 1362 | 3556 | 0.43 | 4.86 | 2273 | 7747 | 1.02 | 0.41 |
| | | CV % | 49.3 | 43.7 | 22.8 | 53.0 | 37.8 | 25.5 | 31.7 | 19.6 |
| TPI | 0 | N | 10 | 9 | 9 | 9 | 10 | 9 | 9 | 9 |
| | | Mean | 46.5 | 234 | 2.04 | 148.5 | 48.8 | 247 | 2.61 | 128.3 |
| | | SD | 18.3 | 121 | 0.37 | 81.8 | 21.9 | 100 | 0.73 | 58.2 |
| | | CV % | 39.4 | 51.8 | 18.2 | 55.1 | 44.9 | 40.3 | 28.1 | 45.3 |
| | 1 | N | 12 | 11 | 11 | 11 | 11 | 9 | 9 | 9 |
| | | Mean | 93.9 | 380 | 2.33 | 105.1 | 67.8 | 383 | 2.54 | 83.1 |
| | | SD | 40.9 | 193 | 0.68 | 86.1 | 27.9 | 105 | 0.73 | 17.5 |
| | | CV % | 43.5 | 50.9 | 29.3 | 81.9 | 41.1 | 27.5 | 28.7 | 21 |
| | 2 | N | 11 | 10 | 10 | 10 | 10 | 8 | 8 | 8 |
| | | Mean | 100.4 | 494 | 2.42 | 64.8 | 111.7 | 602 | 2.63 | 62 |
| | | SD | 40.2 | 181 | 0.40 | 18.6 | 53.5 | 321 | 0.44 | 32.7 |
| | | CV % | 40.0 | 36.7 | 16.4 | 28.7 | 47.9 | 53.4 | 16.7 | 52.8 |

FTD is an active component showing anticancer activity in the FTD/TPI combination drug, and TPI is a modulator to increase the concentration of FTD in the plasma. Therefore, the FTD concentration in the plasma after repeated administrations is most strongly related to the effect and safety of the FTD/TPI combination drug. The $AUC_{0-12}$ of FTD in patients with mild renal impairment (Cohort 1) and patients with moderate renal impairment (Cohort 2) are higher by about 16% and about 51%, respectively, as compared to that in patients with normal renal function. Thus, the AUC of FTD increases with the deterioration of renal function, and the need for reducing the dose of the FTD/TPI combination drug is suggested for patient with severe renal impairment. The elimination half-time of FTD is 2.40 hours and 3.22 hours in the patient with mild renal impairment and the patient with moderate renal impairment, respectively, and a major prolongation is not seen, as compared to 2.09 hours in the patients with normal renal function. The half-time of FTD is sufficiently short as compared to the administration interval when administrating twice a day, 12 hours, thus the effect of the FTD/TPI combination drug can be maintained by reducing to the appropriate dose without changing the administration interval.

In order to determine the appropriate dose for the patients with severe renal impairment, a regression analysis of oral clearance (CL/F) and creatinine clearance (CLcr) of FTD on Day 12 after administration was performed. The result is shown in FIG. 1.

As shown in FIG. 1, it is possible to approximate the relationship of both parameters to the following power function curve.

$$\text{FTD CL/F (L/hr)} = 0.3432 \times \text{CLcr (mL/min)}^{0.4870}$$

CL/F of FTD in each renal impairment level was calculated from CLcr using this regression equation, further, the ratio of the AUC of FTD to the patient with normal renal function was calculated, and these results were shown in Table 2. At this time, the ratio was calculated using a median CLcr (109 mL/min) of the patient with normal renal function as a control (1.00). It is suggested that the AUC of FTD when administering the FTD/TPI combination drug to the patient with severe renal impairment in 15 mg/m², 20 mg/m² and 25 mg/m² is similar to the AUC when administering 35 mg/m² to the patients with normal renal function, the patients with mild renal impairment, and the patients with moderate renal impairment. On the other hand, it is considered that, when administering the FTD/TPI combination drug in 35 mg/m² as it is to the patient with severe renal impairment, the AUC of FTD is increased to more than twice of the patients with normal renal function.

TABLE 2

Range of FTD oral clearance estimated from power regression equation and range of AUC in each dose

| | CLcr (mL/min) | | | FTD CL/F on Day 12 (L/hr) | | | Dose (mg/m²) | AUC ratio to Control | | |
|---|---|---|---|---|---|---|---|---|---|---|
| | Min | Mid | Max | Min | Mid | Max | | Min | Mid | Max |
| Normal | 90 | 109 | | 3.07 | 3.37 | | 35 | 1.10 | 1.00 | |
| Mild | 60 | 75 | 89 | 2.52 | 2.81 | 3.05 | 35 | 1.34 | 1.20 | 1.10 |
| Moderate | 30 | 45 | 59 | 1.80 | 2.19 | 2.50 | 35 | 1.87 | 1.54 | 1.35 |
| Severe | 15 | 22.5 | 29 | 1.28 | 1.56 | 1.77 | 15 | 1.13 | 0.92 | 0.82 |
| | | | | | | | 20 | 1.50 | 1.23 | 1.09 |
| | | | | | | | 25 | 1.88 | 1.54 | 1.36 |

In the safety profile of this test, any of the patient with normal renal function, the patient with mild renal impairment, and the patient with moderate renal impairment was tolerable to 35 mg/m² of the FTD/TPI combination drug. Therefore, any of the AUC of FTD when administering the FTD/TPI combination drug to the patient with severe renal impairment in 15 mg/m², 20 mg/m² and 25 mg/m² is tolerable level. However, there is a possibility that the AUC of FTD when administered in 15 mg/m² is lower than the AUC of the patient with normal renal function, and the effect is attenuated. On the other hand, since renal function of the patient with severe renal impairment is unstable, there is a possibility that the AUC of FTD exceeds the prediction when administering in 25 mg/m². Based on the above, in the patient with severe renal impairment (CLcr: 15 to 29 mL/min), it is most preferred that the FTD/TPI combination drug is administered in 20 mg/m².

In the patient with severe renal impairment, the dose of the FTD/TPI combination drug is reduced to 30 to 50 mg/m²/day as FTD-equivalent, and particularly, reduced to 40 mg/m²/day as FTD-equivalent, whereby efficacy can be expected while maintaining safety.

The invention claimed is:

1. A method for treating cancer which is one of gastrointestinal cancer, large bowel cancer and breast cancer, comprising:

detecting a creatinine clearance of a patient; and
orally administering to the patient with a creatinine clearance of less than 30 mL/min a combination drug comprising α,α,α-trifluorothymidine (FTD) and 5-chloro-6-[(2-iminopyrrolidine-1-yl)methyl]pyrimidine-2,4(1H,3H)-dione hydrochloride in a molar ratio of 1:0.5, a daily dose of 30 to 40 mg/m²/day as FTD-equivalent, divided into two to four portions for administration.

2. The method for treating cancer according to claim 1, wherein the combination drug is administered to the patient with a creatinine clearance of 15 mL/min or more and 29 mL/min or less.

3. The method for treating cancer according to claim 1, wherein a dose of 40 mg/m²/day as FTD-equivalent is divided in two portions.

4. The method for treating cancer according to claim 1, wherein an administration schedule is 5-day consecutive oral administrations and 2-day rest, per week.

5. The method for treating cancer according to claim 1, wherein an administration schedule of 5-day consecutive oral administrations and 2-day rest is repeated twice, followed by rest for 14 days.

6. The method for treating cancer according to claim 1, wherein the cancer is gastrointestinal cancer or breast cancer.

7. The method for treating cancer according to claim 1, wherein the cancer is large bowel cancer.

8. The method for treating cancer according to claim 1, wherein the cancer is gastrointestinal cancer.

9. The method for treating cancer according to claim 1, wherein the cancer is breast cancer.

10. The method for treating cancer according to claim 2, wherein a dose of 40 mg/m²/day as FTD-equivalent is divided in two portions.

11. The method for treating cancer according to claim 2, wherein an administration schedule is 5-day consecutive oral administrations and 2-day rest, per week.

12. The method for treating cancer according to claim 2, wherein an administration schedule of 5-day consecutive oral administrations and 2-day rest is repeated twice, followed by rest for 14 days.

13. The method for treating cancer according to claim 2, wherein the cancer is gastrointestinal cancer or breast cancer.

14. The method for treating cancer according to claim 2, wherein the cancer is large bowel cancer.

15. The method for treating cancer according to claim 2, wherein the cancer is gastrointestinal cancer.

16. The method for treating cancer according to claim 2, wherein the cancer is breast cancer.

17. The method for treating cancer according to claim 3, wherein an administration schedule is 5-day consecutive oral administrations and 2-day rest, per week.

18. The method for treating cancer according to claim 3, wherein an administration schedule of 5-day consecutive oral administrations and 2-day rest is repeated twice, followed by rest for 14 days.

19. The method for treating cancer according to claim 3, wherein the cancer is gastrointestinal cancer or breast cancer.

20. The method for treating cancer according to claim 3, wherein the cancer is large bowel cancer.

21. The method for treating cancer according to claim 3, wherein the cancer is gastrointestinal cancer.

22. The method for treating cancer according to claim 3, wherein the cancer is breast cancer.

23. The method for treating cancer according to claim 4, wherein the cancer is gastrointestinal cancer or breast cancer.

24. The method for treating cancer according to claim 4, wherein the cancer is large bowel cancer.

25. The method for treating cancer according to claim 4, wherein the cancer is gastrointestinal cancer.

26. The method for treating cancer according to claim 4, wherein the cancer is breast cancer.

27. The method for treating cancer according to claim 5, wherein the cancer is gastrointestinal cancer or breast cancer.

28. The method for treating cancer according to claim 5, wherein the cancer is large bowel cancer.

29. The method for treating cancer according to claim 5, wherein the cancer is gastrointestinal cancer.

30. The method for treating cancer according to claim 5, wherein the cancer is breast cancer.

* * * * *